United States Patent

Daculsi et al.

[11] Patent Number: 6,001,394
[45] Date of Patent: Dec. 14, 1999

[54] BIOMATERIAL COMPOSITION AND METHOD FOR PREPARING SAME

[75] Inventors: Guy Daculsi, Vigneux de Bretagne; Pierre Weiss, Nantes; Anne Dupraz, Redon, all of France; Mieczyslam Lapkowski, Zabrze, Poland

[73] Assignee: Centre National de la Recherche Scientifique (C.N.R.S.), Paris, France

[21] Appl. No.: 09/011,215

[22] PCT Filed: Jul. 29, 1996

[86] PCT No.: PCT/FR96/01196

§ 371 Date: Apr. 13, 1998

§ 102(e) Date: Apr. 13, 1998

[87] PCT Pub. No.: WO97/05911

PCT Pub. Date: Feb. 20, 1997

[30] Foreign Application Priority Data

Aug. 7, 1995 [FR] France ................................... 95 09582

[51] Int. Cl.[6] ........................................................ A61K 9/14
[52] U.S. Cl. ........................ 424/489; 424/494; 424/426; 424/423
[58] Field of Search .................................... 424/423, 426, 424/489, 494

[56] References Cited

U.S. PATENT DOCUMENTS 5,717,006   2/1998   Daculsi et al. ........................... 424/426

FOREIGN PATENT DOCUMENTS

| 0 511 868 | 11/1992 | European Pat. Off. . |
| 3 011006 | 1/1991 | Japan . |
| 2 248 232 | 4/1992 | United Kingdom . |
| 86/01113 | 2/1986 | WIPO . |
| 95/21634 | 8/1995 | WIPO . |

*Primary Examiner*—Thurman K. Page
*Assistant Examiner*—William E. Benston, Jr.
*Attorney, Agent, or Firm*—Young & Thompson

[57] ABSTRACT

A biomaterial composition for the resorption/substitution of organic supporting tissues, including 20–75 wt. % of an inorganic phase consisting of particles that include either hydroxyapatite (A) optionally mixed with tricalcium phosphate β (B), or calcium-titaniumphosphate $(Ca(Ti)_4(PO_4)_6)$ (C), and 80–25 wt. % of a liquid phase including an aqueous solution of a water-soluble biocompatible polymer that is cross-linkable under the effect of the pH of the medium. The composition is sterilizable, injectable and curable in biological media to form a biomaterial for replacing supporting tissues.

14 Claims, 1 Drawing Sheet

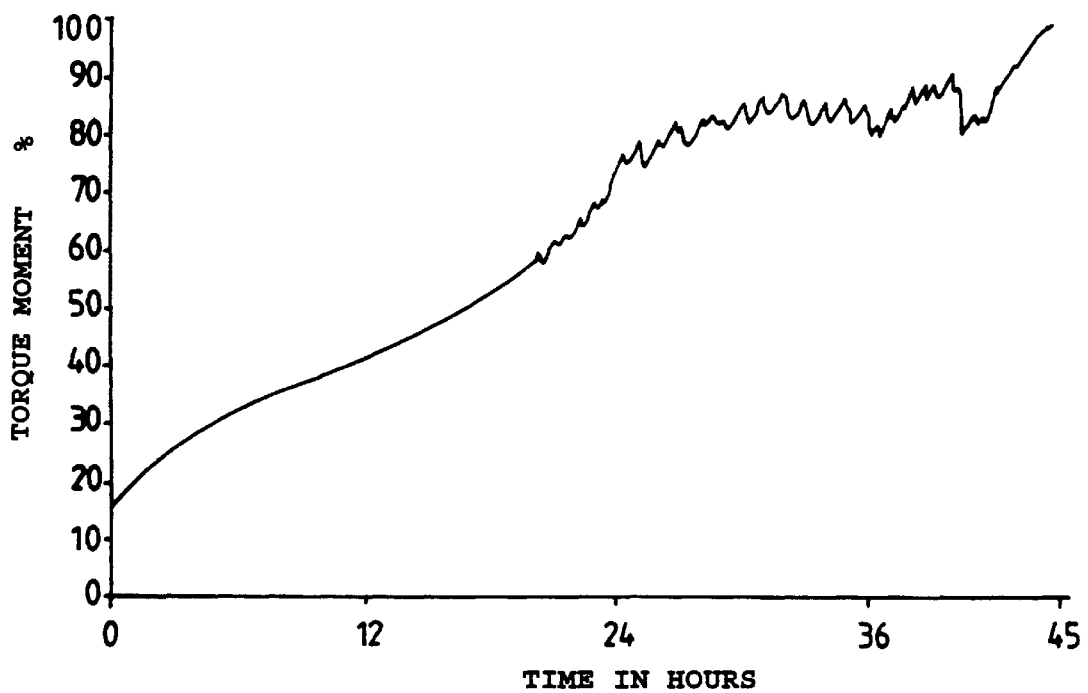

BIOMATERIAL COMPOSITION AND METHOD FOR PREPARING SAME

This application is a 371 of PCT/FR96/01196 filed Jul. 29, 1996.

FIELD OF THE INVENTION

The invention relates to an injectable composition for a biomaterial for filling supporting organic tissues, intended to give rise to a resorption/substitution function.

BACKGROUND OF THE INVENTION

Bony substitutes based on calcium phosphate particles and a biological adhesive are known from the state of the art.

Thus, G. Daculsi et al. have described in Ann. Oto. Rhino. Laryngol. 101:1992 the effectiveness of a calcium phosphate two-phase microporous composition for obliterating the mastoid cavity.

The same authors have also reported the effectiveness of a two-phase calcium phosphate macroporous composition for surgical repair of long bones (Journal of Biomedical Materials Research, Vol. 24, 379–396) and in vertebral arthrodeses (Clinical Orthopaedics and Related Research, 248, 1989, 169–175).

The usefulness of calcium phosphates in odontology has been demonstrated in a number of articles: A. Jean et al. in Cells and materials 1993; 3: 193–200. "Pulpal response to calcium phosphate materials. In vivo study of Calcium Phosphate materials in Endodontics"; B. Aliot-Licht et al. in Arch. Oral Biol. 1994; 39: 481–489 "Comparative effect of calcium hydroxide and hydroxyapatite on the cellular activity of human pulpal fibroblasts. An in vivo approach."

Furthermore, JP 3 011 006 describes a cement for hard tissues including an inorganic phase consisting of at least 60% of alpha tricalcium phosphate and of hydroxy-apatite and/or a calcium monophosphate, and a liquid phase including carboxymethyl cellulose.

However, such a composition exhibits the disadvantage, due to the excessive solubility of $\alpha$ tricalcium phosphate, of not being sufficiently stable to permit a process of resorption/substitution of the hard tissue. Furthermore, such a composition is liable to give rise to detrimental inflammatory processes. Furthermore, this mixture constitutes a calcium ionomer which is not suitable for injection after a few minutes, due to hardening of the mixture as soon as it is made up. This combination exhibits a double instability, a contraction in volume with release of water after several days and, above all, a drop in viscosity after sterilization of the mixture in the autoclave. It does not make it possible to produce a material which is "ready for use", sterile and injectable.

OBJECT OF THE INVENTION

The object of the present invention is to provide a biomaterial composition filled with mineral phase, capable of being reinhabited, injectable and curing in situ in the implantation site.

In particular, this composition must exhibit the following properties:

it must be sterilizable;

it must not be toxic in vivo;

it must have a high mineral filling inducing a mineralization front and/or a tissue cicatrization;

it must include a dispersing agent acting as a vector which carries the mineral filler into the operating site and which then holds it at this site until the tissue cicatrization, while acting as a matrix for composite material;

it must be capable of being introduced into a biological medium, especially by injection with a syringe or an apparatus of "lentula" type employed in dental surgery (a so-called lentulable composition), in the fluid or pasty state, before curing in contact with the buffered biological fluids;

it must be stable in order to be capable of being stored for a relatively long time before use;

it must be easy to use.

SUMMARY OF THE INVENTION

This objective has been attained by the present invention, the subject-matter of which is a composition for a biomaterial for resorption/substitution of supporting organic tissues, comprising:

20 to 75% by weight of an inorganic phase consisting of particles including either hydroxyapatite (A), optionally mixed with $\beta$ tricalcium phosphate (B), or calcium titanium phosphate ($Ca(Ti)_4(PO_4)_6$) (C), and 80 to 25% by weight of a liquid phase including an aqueous solution of a water-soluble, biocompatible polymer self-crosslinkable under the effect of the pH of the medium.

The inorganic phase based on particles of calcium phosphate(s) provides the mineral filler needed for the mineralization front.

The calcium titanium phosphate (CTP) of formula $Ca(Ti)_4(PO_4)_6$ is preferably of the "Nasicon-like" calcium metal phosphate type.

The inorganic particles advantageously include a mixture of hydroxyapatite (A) and of $\beta$ tricalcium phosphate (B), these mixtures being commonly referred to by the acronym BCP (biphasic calcium phosphate). The mixture preferably includes the compounds A and B in an A/B weight ratio of between 80/20 and 30/70, in particular of approximately 60/40.

This latter type of filler consists of a high-temperature frit, ground and classified into powder or into granules whose particles have a diameter of 80 $\mu$m to 200 $\mu$m when the composition is prepared. Other types of synthesis of fillers or of other particle sizes may, however, be selected, depending on the tissues and the indications. The choice of the particle diameter may be guided in particular by the desired resorption kinetics and rheology. Particles of diameter smaller than 80 $\mu$m generally have fairly rapid resorption kinetics. They find their application especially in orthopaedic surgery. For endodontic applications in dental surgery, particles of diameter greater than 200 $\mu$m should be avoided because they pose problems on injection, due to the rheology of the composition.

Other mineral fillers may also be employed, such as the "Nasicon-like" ceramics (CZP), phosphocalcium ceramics or bioglasses.

The liquid phase is used, on the one hand, as a dispersing agent for the particulate mineral filler, capable of mixing intimately with the latter, it being possible for the final composition to be in a liquid or more or less pasty form. On the other hand, it is intended to form a matrix of composite material incorporating the mineral filler.

For this purpose the liquid phase includes a polymer which is self-crosslinkable in aqueous solution.

Bearing in mind the application to a biomaterial, the polymer must be biocompatible, that is to say that it must not be toxic and must not result in a rejection reaction when it is implanted into the organism. Furthermore, its crosslinking must not release any toxic by-product.

In addition, the polymer must be stable in the uncrosslinked state in a given medium and self-crosslinkable merely by being brought into contact with the biological medium into which it is implanted. The polymers which best meet this criterion are those which can crosslink under the effect of the pH of the buffered biological fluids. These polymers are preferably soluble in the uncrosslinked state in a relatively basic aqueous phase, and crosslink under the effect of a drop in pH.

It is particularly advantageous that the polymer should crosslink covalently in the implantation medium, to produce a strong crosslinked biomaterial.

Consequently, preference is given to polymers which, at the pH of the medium, are capable of undergoing a chemical reaction resulting in the formation of intermolecular and possibly intramolecular covalent bonds.

Such polymers may be advantageously selected from polymers having side groups containing silicon-based reactive functional groups, such as alkali metal or ammonium silanolate groups or organosilicon groups which can be hydrolysed in the biological medium to form silanolates without releasing any toxic product as hydrolysis by-product.

A suitable silanolate side group may be, for example, a group of formula

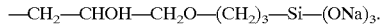

—$CH_2$—CHOH—$CH_2$O—$(CH_2)_3$—Si—$(ONa)_3$.

To provide a degree of crosslinking that is suitable for the application to a curing biomaterial, it is desirable that the silicon-carrying side groups of silanolate or silanolate precursor type should represent from 1 to 5% of the total dry weight of the said polymer.

The base polymer to which the side groups are bonded may be of various natures, provided that it is biocompatible.

It may be advantageously selected from cellulose and polymers derived from cellulose, whose compatibility is well known and applied in galenics to the delay matrices for medication. Nonionic cellulose ethers may be mentioned in particular, for example hydroxyethyl cellulose, hydroxyethyl methyl cellulose or hydroxypropyl methyl cellulose.

Thus, a polymer which is self-crosslinkable by covalent bonds and derived from cellulose may be obtained by etherification of cellulose or of a derivative thereof by reaction with a compound of formula (1)

$$XSi(OZ)_3 \quad (1)$$

where X denotes a halogen atom or a hydrocarbon group containing an epoxy functional group, especially $C_{2-20}$, and Z is selected from a hydrogen atom, an alkali metal and an alkyl group, especially $C_{1-5}$.

The compound of formula (1) may be, for example, (3-glycidoxypropyl)trimethoxysilane

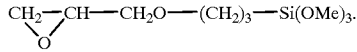

The synthesis of polymers derived from hydroxyethyl cellulose (HEC) and from (3-glycidoxypropyl) trimethoxysilane is described by Arjun C. Sau and Thomas G. Majewicz in Cellulose Ethers; Self-cross-linking mixed ether silyl derivatives, ACS Symp. Ser. 1992, Vol 476, 265–72.

In a basic medium the organosilicon compound is grafted onto the HEC with opening of the epoxide, and the methoxysilane groups are hydrolysed, to produce a polymer corresponding to the simplified formula:

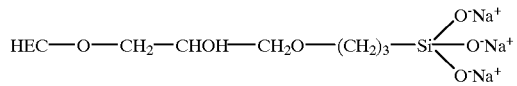

This polymer is stable in aqueous solution at a pH higher than or equal to approximately 10.5. Acidification of the solution results in a gradual increase in viscosity and the formation of a hydrogel. This physical phenomenon corresponds to the crosslinking of the polymer by (i) conversion of the silanolate groups into silanol groups:

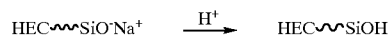

and then formation of a threedimensional network by (ii) condensation of a silanol with another silanol

and/or (iii) condensation of a silanol with a hydroxyl group of the rings of the cellulose ethers or of the substituents

This crosslinking of covalent type, produced by a drop in the pH of the aqueous solution of the polymer, is reversible and the hydrogel redissolves when the pH of the medium is increased.

Such a polymer can be in the dissolved state in a composition according to the invention containing BCP, by virtue of the basicity of these calcium phosphate mixtures. The composition may also contain a base of any type in order to provide the alkalinity needed for dissolving the polymer.

In the composition according to the invention an auxiliary crosslinking of ionic type can also take place at the silanolate groups bridged via the divalent $Ca^{2+}$ cations.

The functionalization by self-crosslinking silanolate groups can be applied to any other type of water-soluble and biocompatible polymer exhibiting a suitable reactivity. Other polysaccharides may be mentioned, especially guar, starch and their etherified derivatives.

Because of its two components, the composition according to the invention forms a system which has a high mineral filling, and is self-crosslinking in contact with buffered biological media, without any adjuvant or catalytic system for bridging, the crosslinking of the polymer being triggered by the change in the pH of the composition.

The crosslinked material obtained will be more or less dense, depending on the polymer content and the quantity of crosslinkable functional groups in the said polymer.

The liquid phase also determines behaviour with regard to the rheological properties and therefore to the viscoelasticity of the uncrosslinked final composition intended to be implanted in the biological medium.

To this end, the concentration of self-crosslinkable polymer is advantageously between 1 and 5% by weight, preferably approximately 2% by weight relative to the weight of the liquid phase.

In an alternative form the liquid phase of the composition may additionally include a noncrosslinkable biocompatible polymer, and this makes it possible independently to determine the rheological properties of the composition before injection and the degree of hardening of the material implanted in the medium. Any water-soluble biocompatible polymer may be employed for this purpose, especially polysaccharides or derivatives such as cellulose and cellulose ethers. The relative proportions of the polymers will be adjusted conventionally as a function of the desired properties.

The composition according to the invention is obtained by mixing the constituents of the inorganic phase and of the liquid phase.

The β tricalcium phosphate and hydroxyapatite or CTP granules or powder of the inorganic phase may be obtained as described by Daculsi et al. (Rev. Chir. Orthop., 1989, 75 (2): 65–71).

A major advantage of the composition according to the invention is that it is sterilizable, before or after the mixing of the two phases.

The invention therefore also has as its subject a composition as described above and sterile.

Conventional sterilization with ethylene oxide is not possible in the case of such a "ready-for-use" material. The components of the mixture must, in fact, be sterilized in their dry form, and this demands handling by the surgeon before the injection. This handling is difficult and not reproducible.

According to the invention the preparation of a sterile composition is carried out by dissolving the polymer constituent of the liquid phase in water to a viscosity determined as a function of the desired final viscosity. The solution obtained is next mixed with the inorganic phase and the resulting composition is introduced into packaging bottles which are sealed and sterilized in the autoclave at 121° C. for 20 minutes.

Depending on the requirements, the autoclave sterilization of the mixture may also be performed at a temperature of 130° C. for 30 minutes if the dissolving potential of the filler is not too great.

The initial viscosity of the composition (polymer concentration) must be adapted to obtain the desired viscosity after sterilization, that is to say the polymer concentration as defined above.

If the dissolving potential of the phosphocalcium filler does not allow the mixture to be sterilized at 121 or 130° C. because of rheological problems at this temperature, the aqueous liquid phase is sterilized in the autoclave separately from the filler in one of the above conditions, and then the mixing of both sterile parts is performed in a sterile white room.

The invention also relates to a kit for the preparation of a composition for a biomaterial, including, on the one hand, a sterile inorganic phase and, on the other hand, a sterile liquid phase, as described above, which are intended to be mixed extemporaneously under sterile atmosphere before implanting.

The composition according to the invention can be stored in its ready-for-use mixed or ready-for-mixing separate form without appreciable loss in quality.

The composition according to the invention may be employed as material for bony filling of supporting organic body tissues, this material being intended to give rise to a resorption/substitution function. It may in particular be employed as a filling material in combination with joint implants or prostheses or for any surgical application and indication requiring some "toughness" or mechanical properties.

Another subject of the invention is therefore a process for the treatment of the human or animal body, including the administration by injection of a composition according to the invention at a site which is normally occupied by a supporting organic tissue, to give rise to a function of resorption/substitution of this tissue.

An example of application is dental surgery. The injection may be carried out with the aid of a system comprising a sterilizable syringe and end fittings provided with plungers for single use, for example the system marketed by Hawe Neos Dental, including a syringe sterilized in the autoclave (Ref. No. 440, Hawe-Centrix C-R®, Mark III syringe) and end fittings (Ref. No. 445).

Another example of application of the composition is orthopaedic surgery, in which it can be injected especially for treating the problems of instability of the lumbar rachis, or as a filling material (sealing agent) used in combination with a joint prosthesis, for example a hip prosthesis. The composition may be injected percutaneously.

BRIEF DESCRIPTION OF THE DRAWING

The curve in the single FIGURE shows the change in the torque moment of a viscometer spring measuring the change in the shear stress as a function of time.

DETAILED DESCRIPTION OF THE INVENTION

An example of composition according to the invention will be given below, the properties of which are illustrated in particular in the single FIGURE which shows the hardening curve of the composition as a function of time in a medium buffered at pH 7 at 25° C.

EXAMPLE OF COMPOSITION

A self-crosslinkable polymer is prepared from a nonionic cellulose ether in the following manner:

An inert nitrogen atmosphere is established in a reactor with magnetic stirring, fitted with a condenser, and 1 l of propanol, 20 g of hydroxyethyl cellulose of high molecular weight (which is insoluble in the propanol) and 1 g of sodium hydroxide are introduced. After one hour's stirring 0.4 g of 3-glycidoxypropyltrimethoxysilane are added to the suspension of cellulose polymer (that is, 2% by weight relative to the weight of polymer).

The mixture is heated for 1 h to 80° C. and then for 2 h under reflux at approximately 110° C.

Stirring is continued overnight without heating and the polymer is then filtered off and then washed with propanol, with acetic acid, with propanol again and finally with acetone.

The silanized polymer is dissolved in a decimolar aqueous solution of sodium hydroxide (pH=13) for 3 days, in a proportion of 2% by weight of dry polymer in the aqueous solvent.

30 g of this liquid phase are mixed with 20 g of a mixture of 40% of β tricalcium phosphate and 60% of hydroxyapatite.

This mixture is placed in filter paper which is in the form of a tube closed at one end, usually employed for an extractor.

The filter filled with the mixture is placed in a vessel containing a buffer solution of 9% NaCl, of pH=7, at a temperature of 25° C., modelling a biological medium. The filter allows ion diffusion between the mixture and the buffer solution.

The curing of the composition due to the drop in pH is followed by measuring the change in the viscosity of the mixture in the course of time, by means of a Brookfield viscometer fitted with a needle No. 29 for small samples, with a slow shear rate of 1 revolution per minute to avoid the rupture of the gel being formed.

The curve in the single FIGURE shows the change in the torque moment of the viscometer spring (measuring the change in the shear stress) as a function of time.

It shows that the mixture cures spontaneously at pH 7 in a progressive manner. With the initial viscosity being 141 Pa s, this reaches 1000 Pa s after 41 hours, whereas the pH of the buffer solution has not changed.

The composition prepared in this example can be sterilized in the autoclave at 121° C. for 20 minutes.

TOXICITY TEST

In a paper in the Journal of Applied Biomaterials Vol. 3, 197–206 (1992), K. P. Andriano et al. have shown the noncytotoxicity of silanes on direct contact of silane-treated mineral fibres with L 929 mouse fibroblast cells.

It is also verified that hydroxyethyl cellulose modified with the epoxysilane is not cytotoxic. Using L 929 cells, direct deposition of the cells on the polymer which is silane-treated and dried into film shows 97 to 99% of living cells after 24 hours in direct contact.

In an indirect (transwell) test, in which the cells are deposited on a layer of gel and the polymer is placed on the other side of the gelled layer, 97 to 98% of living cells are also found again after 24 hours, which shows that the products of diffusion through the gel are not toxic.

The silane-treated polymer is not cytotoxic according to Afnor standard NF S 90 702.

We claim:

1. A composition for a biomaterial for resorption/substitution of supporting organic tissues, comprising:
   20 to 75% by weight of an inorganic phase consisting of particles including either hydroxyapatite (A), optionally mixed with β tricalcium phosphate (B), or calcium titanium phosphate $(Ca(Ti)_4(PO_4)_6)$ (C), and
   80 to 25% by weight of a liquid phase including an aqueous solution of a water-soluble, biocompatible polymer self-crosslinkable under the effect of the pH of the medium.

2. The composition according to claim 1, wherein said inorganic phase comprises a mixture of hydroxyapatite (A) and of β tricalcium phosphate (B) in an A/B weight ratio of 80/20 to 30/70.

3. The composition according to claim 1, wherein said inorganic phase comprises a mixture of hydroxyapatite (A) and of β tricalcium phosphate (B) in an A/B weight ratio of approximately 60/40.

4. The composition according to claim 1, wherein said inorganic phase consists of a powder whose particle size when the composition is prepared is between 80 and 200 μm in diameter.

5. The composition according to claim 1, wherein said polymer self-crosslinks forming covalent bonds under the effect of the pH.

6. The composition according to claim 1, wherein said polymer contains side groups of alkali metal or ammonium silanolate or silanolate precursor.

7. The composition according to claim 1, wherein said polymer contains side groups of alkali metal or ammonium silanolate or silanolate precursor, the side groups representing from 1 to 5% of the total dry weight of the said polymer.

8. The composition according to claim 1, wherein said polymer is derived from a polymer selected from the group consisting of cellulose, a nonionic cellulose ether, guar and starch.

9. The composition according to claim 1, wherein said polymer is derived from a polymer selected from the group consisting of cellulose, a nonionic cellulose ether, guar and starch, and said polymer results from the etherification of cellulose or of a derivative thereof with a compound of formula (1) $XSi(OZ)_3$ where X denotes a halogen atom or a hydrocarbon group containing an epoxy functional group, and Z is selected from the group consisting of a hydrogen atom, an alkali metal and an alkyl group.

10. The composition according to claim 1, wherein the concentration of said self-crosslinkable polymer in the liquid phase is from 1 to 5% by weight.

11. The composition according to claim 1, which is sterile.

12. A method for the preparation of a composition for a biomaterial for resorption/substitution of supporting organic tissues, comprising:
   20 to 75% by weight of an inorganic phase consisting of particles including either hydroxyapatite (A), optionally mixed with β tricalcium phosphate (B), or calcium titanium phosphate $(Ca(Ti)_4(PO_4)_6)$ (C), and
   80 to 25% by weight of a liquid phase including an aqueous solution of a water-soluble, biocompatible polymer self-crosslinkable under the effect of the pH of the medium, comprising the following steps:
   preparing a liquid phase by dissolving said polymer in an aqueous solvent,
   mixing said inorganic phase with said liquid phase, and sterilizing the mixture thus obtained.

13. The method according to claim 12, wherein the sterilization is performed in an autoclave at a temperature of 121 or 130° C.

14. A kit for the preparation of a composition according to claim 1, which is sterilized, comprising:
   a sterile inorganic phase consisting of particles including either hydroxyapatite (A), optionally mixed with β tricalcium phosphate (B), or calcium titanium phosphate $(Ca(Ti)_4(PO_4)_6)$ (C), and
   a sterile liquid phase comprising an aqueous solution of a water-soluble, biocompatible polymer self-crosslinkable under the effect of the pH of the medium, which are intended to be mixed extemporaneously under sterile atmosphere before implanting of the composition.

* * * * *